United States Patent
Kucharczyk et al.

(10) Patent No.: US 7,670,327 B2
(45) Date of Patent: Mar. 2, 2010

(54) CATHETER SYSTEMS FOR DELIVERY OF AGENTS AND RELATED METHOD THEREOF

(75) Inventors: John Kucharczyk, Bishop, GA (US); George T. Gillies, Charlottesville, VA (US)

(73) Assignees: Regents of the University of Minnesota, Minneapolis, MN (US); University of Virginia Patent Foundation, Charlottesville, VA (US)

( * ) Notice: Subject to any disclaimer, the term of this patent is extended or adjusted under 35 U.S.C. 154(b) by 650 days.

(21) Appl. No.: 11/105,166

(22) Filed: Apr. 13, 2005

(65) Prior Publication Data
US 2005/0245896 A1 Nov. 3, 2005

Related U.S. Application Data

(60) Continuation-in-part of application No. 10/444,884, filed on May 23, 2003, which is a division of application No. 09/574,857, filed on May 19, 2000, now Pat. No. 6,599,274, application No. 11/105,166.

(60) Provisional application No. 60/177,263, filed on Jan. 20, 2000, provisional application No. 60/561,571, filed on Apr. 13, 2004.

(51) Int. Cl.
*A61M 31/00* (2006.01)

(52) U.S. Cl. .................... 604/500; 604/522

(58) Field of Classification Search ............ 604/39–45, 604/522, 500, 506–508
See application file for complete search history.

(56) References Cited

U.S. PATENT DOCUMENTS 3,771,527 A 11/1973 Ruisi .................. 604/43

(Continued)

OTHER PUBLICATIONS

Chen, Z.-J., et al., "Intraparenchymal Drug Delivery via Positive Pressure Infusion: Experimental and Modeling Studies of Poroelasticity in Brain Phantom Gels," IEEE Transactions on Biomedical Engineering, 49(2), 85-96, (Feb. 2002).

(Continued)

*Primary Examiner*—Nicholas D Lucchesi
*Assistant Examiner*—Theodore J Stigell
(74) *Attorney, Agent, or Firm*—Mark A. Litman & Associates, P.A.

(57) ABSTRACT

A method is disclosed for the delivery of therapeutic agents into tissues, blood vessels, and body ducts of the human body. A novel catheter enables controlled directing of emitted drug delivery to assist control of drug dwell time in targeted areas. One coaxial catheter embodiment provides capability for locating an outer lumen of the system into the target region, with localization of said outer lumen carried out by use of appropriate medical imaging modalities. In one embodiment, an inner lumen of the catheter means is primed with the agent to be delivered, and recirculated flow of the agent through pluralities of appropriately positioned port holes on the two lumens then occurs via one or more active and/or passive flow driving and guiding techniques intrinsic to the design of the coaxial catheter system. Another coaxial catheter embodiment carries and emits agent in an outer cannula and recaptures agent plus liquid or fluids in the body (such as blood, bile, serum, stable (non-flowing) liquid or kinetic liquid) in an inner cannula.

20 Claims, 5 Drawing Sheets

U.S. PATENT DOCUMENTS

| | | | |
|---|---|---|---|
| 3,929,126 A | 12/1975 | Corsaut | 604/43 |
| 5,211,165 A | 5/1993 | Dumoulin et al. | 600/410 |
| 5,318,518 A * | 6/1994 | Plechinger et al. | 604/43 |
| 5,487,739 A | 1/1996 | Aebischer et al. | 604/890.1 |
| 5,624,413 A | 4/1997 | Markel et al. | 604/523 |
| 5,709,874 A | 1/1998 | Hanson et al. | 424/423 |
| 5,718,678 A | 2/1998 | Fleming, III | 604/43 |
| 5,718,692 A | 2/1998 | Schon et al. | 604/264 |
| 5,720,720 A | 2/1998 | Laske et al. | 604/500 |
| 5,744,958 A | 4/1998 | Werne | 324/318 |
| 5,776,111 A | 7/1998 | Tesio | 604/264 |
| 5,947,953 A | 9/1999 | Ash et al. | 604/508 |
| 6,026,316 A | 2/2000 | Kucharczyk et al. | 600/420 |
| 6,030,358 A | 2/2000 | Odland | 604/27 |
| 6,061,587 A | 5/2000 | Kucharczyk et al. | 600/411 |
| 6,198,966 B1 | 3/2001 | Heruth | 604/20 |
| 6,228,046 B1 | 5/2001 | Brisken | 604/22 |
| 6,272,370 B1 | 8/2001 | Gillies et al. | 600/411 |
| 6,312,444 B1 | 11/2001 | Barbut | 606/200 |
| 6,379,378 B1 | 4/2002 | Werneth et al. | 607/105 |
| 6,409,700 B1 | 6/2002 | Siegel, Jr. et al. | 604/43 |
| 6,533,763 B1 | 3/2003 | Schneiter | 604/264 |
| 6,537,241 B1 | 3/2003 | Odland | 604/9 |
| 6,599,274 B1 | 7/2003 | Kucharczyk et al. | 604/264 |
| 6,626,902 B1 | 9/2003 | Kucharczyk et al. | 606/41 |
| 6,638,242 B2 | 10/2003 | Wilson et al. | 604/43 |
| 6,645,183 B2 | 11/2003 | Christensen et al. | 604/246 |
| 6,663,596 B2 | 12/2003 | Griego et al. | 604/164.02 |
| 6,663,613 B1 | 12/2003 | Evans et al. | 604/523 |
| 6,676,627 B1 * | 1/2004 | Bonnette et al. | 604/22 |
| 6,758,828 B2 | 7/2004 | Hammer et al. | 604/43 |
| 6,834,201 B2 | 12/2004 | Gillies et al. | 600/411 |
| 2003/0204171 A1 | 10/2003 | Kucharczyk et al. | 604/264 |

OTHER PUBLICATIONS

Broaddus, W.C., et al., "Advances in Image-Guided Delivery of Drug and Cell Therapies into a Central Nervous System," *Neuroimaging Clinics of North America*, 11(4), 727-735, (Nov. 2001).

Broaddus, W.C. et al., "Strategies for the Design and Delivery of Antisense Oligonucleotide in Central Nervous System," *Methods in Enzymology: Antisense Technology, Part. B: Applications*, 314, 121-135 (2000).

Humphrey et al., "Hydrodynamically Unstable Turning Flow in the End-Space of a Magnetically Guided CNS Catheter," in Kasagi, N., Eaton, J.K., Friedrich, R., Humphrey, J.A.C., Leschziner, M.A. and Miyauchi, T., eds., *Proceedings of the Third International Symposium on Turbulence and Shear Flow Phenomena* (Tokyo Institute of Technology, Tokyo, 2003), pp. 811-816.

\* cited by examiner

CATHETER SYSTEMS FOR DELIVERY OF AGENTS AND RELATED METHOD THEREOF

RELATED APPLICATIONS DATA

This Application is a continuation-in-part application of U.S. patent application Ser. No. 10/444,884, filed May 23, 2003 (U.S. 20030204171, published Oct. 30, 2003), which is in turn a division of U.S. patent application Ser. No. 09/574,857, filed May 19, 2000, now U.S. Pat. No. 6,599,274, which in turn claims priority from U.S. Provisional Patent Application Ser. No. 60/177,263 filed Jan. 20, 2000. This Application independently claims additional priority from U.S. Provisional Application Ser. No. 60/561,571, filed Apr. 13, 2004. This Application also claims priority from U.S. patent application Ser. No. 10/957,538, filed Oct. 1, 2005, titled Combined MR Coil Technology in Medical Devices.

BACKGROUND OF THE INVENTION

1. Field of the Invention

This invention relates to improved means of intravascular, intraparenchymal and intracerebroventricular delivery of agents such as diagnostic agents or therapeutic agents for the treatment of local medical conditions in the head and body. Such treatments and local medical conditions may include, by way of non-limiting examples, neoplasms, the counteraction of neurodegenerative disorders, the recanalization and reperfusion of blocked arterial and venous structures and the treatment of other forms of disease within the vasculature and elsewhere in the body. Systemic delivery of therapeutic agents into the brain is limited by the presence of the blood brain barrier formed by the tight junctions of endothelial cells that line capillaries within the brain. As a result, many diseases and disorders of the central nervous system are inadequately treated by conventional systemic therapies. The search for new approaches for dealing with this problem has lead to the development of positive pressure infusion as a means for delivering therapeutic agents directly into the brain, thereby bypassing the blood brain barrier. A general requirement for targeted delivery of therapeutic drug agents, gene vectors and cells into the brain parenchyma, cerebral fluid compartments or cerebral vasculature is the availability of suitable access devices. The present invention relates to the field of acute or chronic implantable medical devices and catheters in particular. More specifically, the invention relates to a class of catheters that can be used to carry out positive pressure infusions of therapeutic agents into an organ, particularly a solid tissue organ such as a brain, for the purpose of avoiding the restrictive effects of the blood-brain barrier. The invention additionally relates to a class of catheters that can be used to deliver fluids into or remove fluids from within the vasculature of a body. The invention also relates to that class of catheters that are multi-lumen devices. The invention further relates to classes of treatment that may utilize successive delivery of initial and follow-up doses of therapeutic agents, or successive delivery of a first and then subsequent different therapeutic agents, into the same location or set of locations within a body part of a patient or live being such as a brain or a tubular vascular structure of an animal or human being.

2. Background of the Art

There are many instances in which a neurosurgeon, an interventional radiologist, a cardiologist or other clinician would wish to deliver a diagnostic or therapeutic agent into a targeted local area, especially the brain, the cerebral vasculature, the cardiovascular system or elsewhere in the vasculature or the body ducts of a patient, for example, for the treatment of a local condition, such as neoplastic disease or arterial blockages. Potential therapeutic applications for the delivery of such agents would include but not be limited to the delivery of chemotherapeutic and antiangiogenic agents for the treatment of glioblastoma multiforme and other intracranial neoplasms, the delivery of angiogenic drug and gene agents and autologous stem cells into the heart to reverse tissue damage following myocardial infarcts, and the delivery of antithrombolytic agents into the peripheral vasculature to break up thrombotic and stenotic occlusions and allow for recanalization of arteries and veins and reperfusion of dependent tissues. To enlarge upon one of these applications, consider that positive pressure infusion of agents directly into the bulk brain tissues is a technique that has been taught by several workers, examples of which are Laske, et al., (U.S. Pat. No. 5,720,720), Kucharczyk, et al., (U.S. Pat. No. 6,026,316), and Gillies, et al., (U.S. Pat. No. 6,272,370). The resulting convection-enhanced flow of catheter-delivered infusates through the interstitial space of the brain can provide for regional volumes of distribution of therapeutic agents without the need to have large molecular weight species traverse the blood-brain barrier. Special neurocatheters optimized for this approach to drug delivery are needed in order to maximize the utility of such therapies. This general approach to intraparenchymal therapies also applies to the delivery of autologous stem cells into tissues in the brain and heart for the treatment of neurodegenerative disorders and the sequellae of myocardial infarction, respectively, as well as for infusion protocols for the assessment and treatment of traumatic brain injury.

Specialized multi-lumen therapy-delivery catheter systems have been disclosed by Kucharczyk et al. in U.S. Pat. No. 6,626,902 and in European Patent Application No. 01303108.3-2310. Coaxial catheters for the intraparenchymal delivery of cells and drug agents have been disclosed by Kucharczyk et al. in U.S. Pat. No. 6,599,274 and U.S. patent application Ser. No. 10/444,884 and Gillies has disclosed a catheter means with adjustable port holes for control of regulation of the flow of infused agents into the brain, in U.S. Ser. No. 60/380,387 (abandoned, now 60/645,302). Several clinical and pre-clinical applications of various types of therapy delivery catheters are discussed in the articles of Chen, Z.-J., et al., "Intraparenchymal Drug Delivery via Positive Pressure Infusion: Experimental and Modeling Studies of Poroelasticity in Brain Phantom Gels," *IEEE Transactions on Biomedical Engineering*, 49 (2), 85-96, (February 2002); Broaddus, W. C., et al., "Advances in Image-Guided Delivery of Drug and Cell Therapies into the Central Nervous System," *Neuroimaging Clinics of North America*, 11 (4), 727-735, (November 2001); and Broaddus, W.C., et al., "Strategies for the Design and Delivery of Antisense Oligonucleotide in Central Nervous System," *Methods in Enzymology: Antisense Technology, Part. B: Applications*, 314, 121-135 (2000).

One limitation of the art is that none of the catheters known to have been developed to date, nor many others of those foreseen in the literature have been optimized in design for the localized control of dwell time of delivered agent during a targeted delivery. The dwell time refers to the time (actually a concentration over time) for which the agent remains at a satisfactorily active level at the location where it is intended to be active. In particular, there has been no optimization of recirculation of the infused agent in ways that do not damage the adjacent tissues if the agent is being delivered intraparenchymally, or in ways that do not restrict blood flow if the agent is being delivered inside the vasculature. This would be a desirable feature, especially in instances where the infusate might otherwise simply be carried away by the local flow of blood, thus permitting only a limited dwell-time of it in the target zone of interest. Among those catheters claiming some form of recirculative capabilities is that described by Evans et al. (U.S. Pat. No. 6,663,613) which teaches a certain method of rotary arterectomy that might be carried out in concert with the recirculation of antithrombolytic agents within the lumen of a blood vessel. The technique is limited in that balloons, filters or other shielding means must be positioned on either side of the recirculation zone in order to contain the agent. The blockage of local blood flow cannot be tolerated indefinitely, nor can such means be extended into solid tissues of the brain without damage to those tissues. The device described by Barbut (U.S. Pat. No. 6,312,444) suffers from a similar limitation. The system of Heruth (U.S. Pat. No. 6,198,966) is further limited in that once the agent exits the distal tip of the catheter, it cannot recirculatively return into it, even though the flow of the agent within the catheter can circulate internally through the device in a continuous manner. A still further-related limitation is that found in the catheter of Wernerth et al. (U.S. Pat. No. 6,379,378) in which the recirculative flow of a working fluid inside the catheter is able to modulate the temperature-dependent performance characteristics of a urokinase antithrombolytic agent, but without the agent itself being able to recirculate through the catheter in order to re-treat a region of vascular stenosis.

A second limitation of the existing art is that many types of multi-lumen implantable devices that are suitable, e.g., for recirculative hemodialysis are nevertheless not configured in such a way that a given volume of therapeutic agent could recirculatively flow into and out of a user-selected region in the distal tip of the device. This limitation applies to the devices disclosed in U.S. Pat. Nos. 5,624,413 (Markel et al.); U.S. Pat. No. 5,718,692 (Schon); U.S. Pat. No. 5,776,111 (Tesio); U.S. Pat. No. 5,947,953 (Ash et al.); and U.S. Pat. No. 6,638,242 (Wilson et al.).

A third limitation of the art is that the existing multi-lumen catheter designs do not describe pumping means for coordinately controlling emitting flow and recapture flow of agents, such as would enabling recirculative flow between the outside of an outermost lumen and the inside of an interior or innermost lumen. This is the case, for instance, in the device disclosed by Fleming (U.S. Pat. No. 5,718,678). In those cases where the existing multi-lumen catheter designs do allow for at least dialysis-like exchange of fluids between an outer lumen and tissues external to it, they would still be essentially nonfunctional in situations where there was substantial flow of a fluid around the outer lumen, as when the catheter is inserted into a blood vessel. Such a limitation applies for instance to the device disclosed by Odland (U.S. Pat. No. 6,537,241). A still further example of a related limitation is that suffered by the device of Hanson et al. (U.S. Pat. No. 5,709,874) which is able to deliver an agent into the boundary layer of the flow occupying the region between the inner lumen of the blood vessel and the vessel wall, but which is not able to recirculate the agent in order to increase its dwell time in the boundary layer region.

A fourth limitation in certain classes of the existing art is that the intra-tube flow dividers inside of some types of multi-lumen devices seals at the end of the catheter in such a way that there cannot be communication between the input and output channels. This is the case in the blood recirculation catheter of Siegel et al. (U.S. Pat. No. 6,409,700).

A fifth limitation of the existing art is that in catheters incorporating either active or passive flow control devices in their distal tips, the pressure gradients that are established are such as to preclude efficient recirculative flow. An example of the former is the device and system of Brisken (U.S. Pat. No. 6,228,046) and an example of the latter is that described by Schneiter (U.S. Pat. No. 6,533,763). A further limitation of passive flow control devices is that which arises in the device disclosed by Christensen et al. (U.S. Pat. No. 6,645,183) in which the length of the catheter alone is used to control the flow rate at a constant pressure, but no provision is made for recirculating the flow in the distal region of the device.

Another limitation in the prior art is that single port catheters provide only limited distribution of drugs because the effective radius of drug penetration of the drug agent is restricted. Attempts to overcome this problem by increasing the volume rate of delivery of the drug through a single port can result in unintended damage to brain cells and nerve fibers. Another aspect of this invention, therefore, is to overcome the inherent agent distribution limitations of single point drug delivery by devising a multi-lumen catheter with multiple drug release sources which under positive pressure delivery effectively disperse over an appropriate tissue region containing receptors for the drug agent.

Further examples of prior art in the field of the invention include U.S. Pat. No. 6,663,596 (Griego et al.), which discloses a coaxial catheter means for mixing chemical species in the distal tip of the catheter means in preparation for delivery of it into a body part through the catheter means, but not in a recirculative fashion; U.S. Pat. No. 6,834,201 by Gillies et al., discloses a coaxial catheter means in which there is a reversing flow from the inner tube to the outer tube, within the distal tip of the catheter means but not in a recirculative fashion relative to fluids in regions exterior to the distal tip of the catheter means; and Humphrey et al., "Hydrodynamically Unstable Turning Flow in the End-Space of a Magnetically Guided CNS Catheter," in Kasagi, N., Eaton, J. K., Friedrich, R., Humphrey, J. A. C., Leschziner, M. A., and Miyauchi, T., eds., *Proceedings of the Third International Symposium on Turbulence and Shear Flow Phenomena* (Tokyo Institute of Technology, Tokyo, 2003), pp. 811-816, who describe the fluid dynamics of the reversing flow that occurs in one embodiment of the device disclosed by Gillies et al. in U.S. Pat. No. 6,834,201, but who also do not describe a recirculative therapy delivery system.

None of the multi-lumen intraparenchymal therapy delivery devices extant in the art overcome these limitations, nor does the prior art describe means, techniques, and systems for improving the designs of them such that these limitations would not prevent successful therapeutic protocols from being carried out.

There are numerous catheter designs that contain multiple lumens for parallel or adjacent flow of liquids, but none are believed to address capture and recirculation of materials for redlivery. For example, U.S. Pat. No. 6,758,828 (Hammer) describes an apparatus that delivers an agent to a treatment region, the apparatus having an outer cannula or lumen that has an internal surface and an external surface, the external surface being substantially smooth to penetrate tissue whereas the distal end is tapered; an inner cannula, or lumen coaxial to the outer cannula, providing a common fluid path (that is the same fluid passes through both the inner cannula and outer cannula) at the distal end with the inner surface of the outer cannula; a source of fluid to be passed through the common fluid path, the source of fluid comprising at least a reservoir of nutrients and/or gases for maintaining cells contained in a lumen coaxial and internal to the inner cannula; a semipermeable membrane comprises the surface of the lumen, thus allowing controlled material transport across the lumen surface; a source of cells or other biologically active material mass flow connected to the proximal lumen so that the cells or other biologically active material can exit the distal portion upon entering the target tissue; and a first flow distributor located at the proximal end of the outer cannula to provide substantially uniform flow through the outer cannula.

U.S. Pat. No. 6,030,358 (Odland) describes an apparatus having a pump reservoir and one or more microcatheters, for use in delivering and/or recovering fluid to and/or from a tissue site or for performing tissue engineering outside of the body.

Significant and potentially useful advances in the treatment of intracranial neoplasms, traumatic brain injury, neurodegenerative disorders, sequellae from myocardial infarcts, and coronary and peripheral vascular diseases could be realized if alternatives to the prior art were to be able to demonstrate safety and efficacy via improvement of the catheter systems used for recirculative delivery of therapeutic agents. The present invention discloses a means, technique, and system for attempting to reach this goal by implementation of a novel set of catheter means that traverse the limitations of the existing art discussed above.

SUMMARY OF THE INVENTION

Process and devices for delivering diagnostic and therapeutic agents into a body part, including at least a parenchymal organ (such as a brain) or a tubular lumen (such as a blood vessel) or a fluid filled compartment (such as the cerebral ventricles) use a novel arrangement of coaxial or coparallel lumens within catheters are disclosed. The catheters comprise a single implantable medical device capable of recirculating the agent within a region of the catheter and/or within a region of the body part. It is possible, through the use of controlled recirculation, to focus agent delivery and minimize non-targeted or specious delivery of agent to non-targeted areas of the patient.

DETAILED DESCRIPTION OF THE INVENTION

Figure 1:
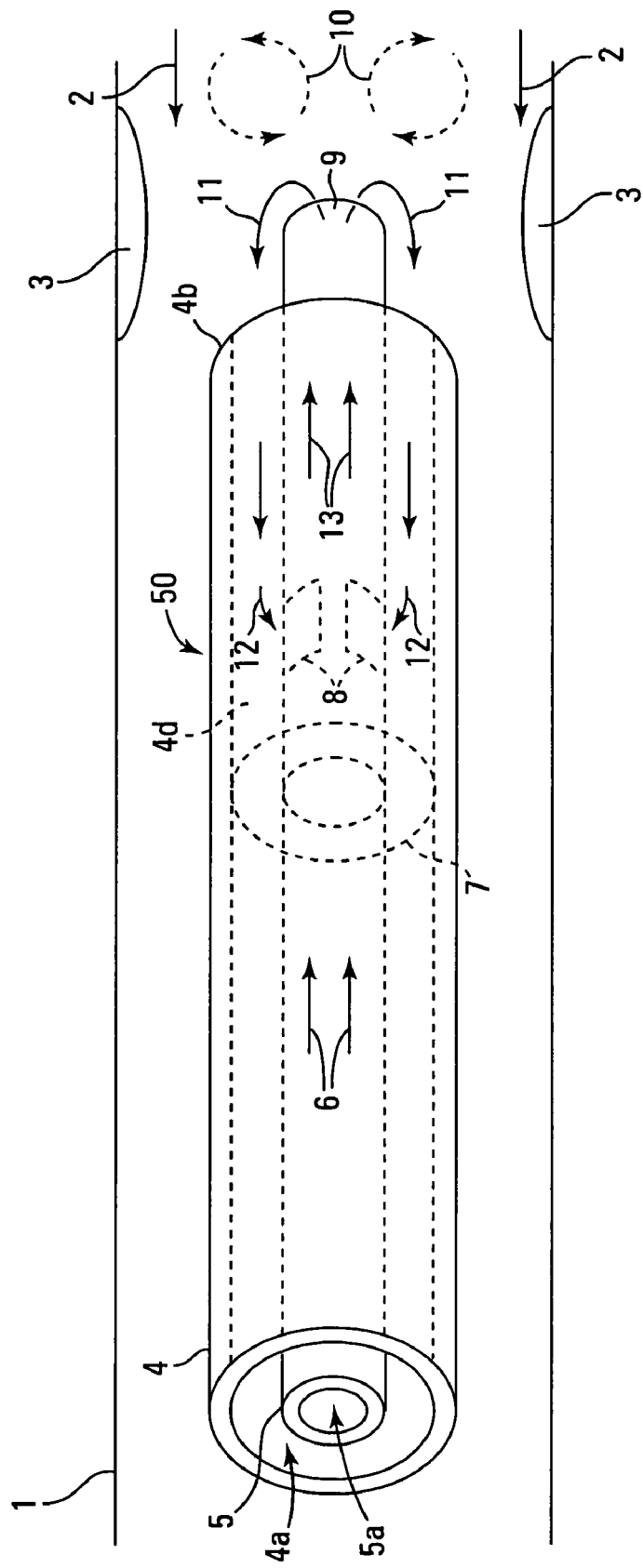
FIG. 1 shows an in situ assembly of one embodiment of a coaxial catheter means used to achieve recirculative delivery of an infused agent in the case where the direction of flow of the agent through the catheter means is anti-parallel to that of the blood of the host vessel.

A number of alternative structures are able to accomplish the above described effects and aspects of the invention. A catheter generally has a distal end (farthest from the point of insertion) and a proximal end (closest to the point of insertion), and has a fixed (or variable) number of outlets and inlets (e.g., vents, tubes, openings, port holes, lumen openings, etc.). The catheter is inserted into a body part of a patient using any means of imaging and guidance deemed appropriate by the clinician and is directed towards a targeted site. Where the intended use of the catheter is to deliver an agent into a blood vessel, the distal end may be directed towards the target site in either a blood flow parallel direction, a blood flow antiparallel direction, or a blood flow neutral direction. The structure of the catheter may desirably be configured to match the relative direction of blood flow (if any) to be encountered at the agent delivery site.

In the design of the catheter structures used to effect the technology described herein, there are at least two scale factors with respect to the release, capture, and recirculation paths for the agent within and external to the outer surface of the catheter. The scale of the catheter release area and capture area is typically comparable to the order of magnitude of or a smaller multiple of or equivalent to the size of the region to be treated (e.g., a tumor, a deposit, or other lesion, etc.). For example, a minimum distance between a release area for the agent and the capture agent for the agent (and blood) could be about 0.5× the length of the region to be treated and up to 10× the length of the region to be treated. This range is useful because the agent may be released (in a parallel direction among blood flow, release area and capture area) at or immediately before the region to be treated, and even if the capture area is only 0.5× the length of the region to be treated, some of the agent will not be recaptured and will flow over the region to be treated. In addition, material adhering to or absorbed in the first contacted region to be treated may diffuse across the region to be treated or picked up by continued blood flow or be deposited further along the region to be treated. The maximum length of a typical type of region to be treated (e.g., a lesion) may be about 3-5 cm maximum. The minimum length of a typical region to be treated might similarly be about 1 mm. The length of distance along the catheter between a release area and a capture area might therefore be approximately 0.5 mm to 50 cm, more likely to be between 1 mm and 10 cm.

A second scale factor to be considered in the design and operation of the catheter and the process of delivery of the agent and recapture of the agent is the time frame over which the material will be released, the dwell time of the agent within the region, and the time when the agent is captured. The wavelength of possible blood flow in the region of the vasculature to be treated is typically about 50-100 beats/minute. The wavelength of the flow of blood (and hence the delivery medium for the released agent) is the distance between peaks in the column of blood flow between pressure peaks. The length of the lesion may be used (from image measurements) to assist in setting the scale factor for length of the treatment range (e.g., release area and capture area) and the inverse of the pulse sets the scale factor for time.

As noted above, there are at least two general cases in which agents are delivered, and therefore there may be at least two distinct classes of the device. One class provides recirculation (either within the catheter or external to the catheter in the region to be treated) in parallel with the blood stream and another antiparallel to the blood flow. In these modes the system can, to some degree capture blood flow and/or reverse the blood flow in a specific region of treatment.

In one non-limiting embodiment, where the intended use of the catheter is to deliver an agent into a blood vessel, wherein the flow of the blood is in the direction opposing the input flow of the agent, the catheter could consist of at least two coaxial tubes, at least an inner tube and a at least a coaxial outer tube, with the agent being delivered through the central barrel of the inner tube. The outer diameter of the inner tube could be significantly smaller than the inner diameter of the outer tube. A sealing ring or baffle could position the distal end of the inner tube within the distal end of the outer tube and prevent reflux flow of any material through the length of the intertube gap. As the agent exits the distal tip of the inner tube, it would encounter the counter-flowing blood stream. Mixing of the agent occurs within the context of the complex flow patterns in that region, which will necessarily vary over relatively short time frames because of pulsed blood flow. Some fraction of the mixture of agent and blood will remain temporarily in the mixing zone, another fraction of it will flow past the distal tip of the catheter system and downstream in the blood vessel, and the remainder of it will flow into the intertube gap between the inner and outer tubes of the catheter. At a location proximal to the sealing ring or baffle, small apertures in the wall of the inner tube will permit the mixture of agent and blood to re-enter the inner tube and be driven by the flow in the inner tube, thus recirculating back into the mixing zone at the end of the distal tip of the inner tube. The recirculative flow can go on indefinitely, until the clinician stops the treatment.

In another, alternative embodiment, where the intended use of the catheter is to deliver an agent into a blood vessel, wherein the flow of the blood is in the same direction as the input flow of the agent, the catheter would consist of two coaxial tubes, with the agent being delivered through the inter-tube gap between the two coaxial tubes. The outer diameter of the inner tube would be significantly smaller than the inner diameter of the outer tube. A sealing plate or baffle would block the inner tube shut at a point proximal to the exit port holes for the agent in the outer tube. The agent would exit the outer tube port holes and mix with the blood flowing in the vessel. The axial location of the outer tube port holes relative to the distal tip of the catheter assembly would be such as to insure that there was sufficient mixing time for the agent and blood, given the blood flow rate at the point of delivery. A fraction of the mixture would continue to flow downstream within the vessel past the distal end of the catheter assemble, but the remainder of the mixture would be diverted back into the catheter assembly via a soft, flexible cap attached to the distal tip of the catheter assembly, which serves to channel the flow into the distal tip of the inner tube. The mixture would exit the inner tube and re-enter the inter-tube gap via apertures in the inner tube positioned distal to the sealing plate or baffle, and proximal to the exit port holes in the outer tube, thus permitting recirculative flow of the mixture.

In still another preferred embodiment, where the intended use of the catheter is to deliver an agent into a blood vessel or another body part or organ, wherein the blood is not flowing or wherein the circulation of some other bodily fluid is in stagnation, the catheter would consist of two coaxial tubes, with the agent being delivered through the inter-tube gap between the two coaxial tubes and exiting through one or more port holes on the distal end of the outer tube. The outer diameter of the inner tube would be significantly smaller than the inner diameter of the outer tube, except at the distal end, where the inner tube would flare upward in diameter in a tapered fashion until it reached the same diameter as the outer tube, thus blocking the outer tube shut at its distal end. Flow from the outer tube port holes would introduce the agent into the region surrounding the distal tip of the catheter, whereupon it could be drawn back into the inner tube by a suction device or pumping means on the proximal end of the inner tube. If the agent were an antithrombolytic material that were used to decompose a stenotic lesion in a blood vessel, then a mixture of the agent plus blood plus the particulate matter that had made up the lesion could be withdrawn from the region surrounding the distal tip of the catheter.

One way of describing the methods and catheters used in the present technology would include a method of delivery of a diagnostic or therapeutic liquid drug solution to a region in a patient comprising:

delivering the agent from a portal from a first fluid pathway in a catheter into a liquid or tissue environment within the patient; allowing the liquid agent to contact a targeted area of treatment within the patient; capturing at least some agent mixed with said liquid from the environment;

returning at least some captured agent mixed with liquid from the environment to a second fluid pathway in the catheter; and delivering at least some captured agent mixed with liquid from the environment outside of the catheter so that the captured agent is delivered to the targeted area of treatment. As previously noted, the agent may be any material desirably introduced into a patient, especially for treatment, but also for diagnosis. Agents to mark clots, anti-inflammatory agents, clot dissolving agents, anti-clotting agents, vascular wall repair agents, antibiotics, cell treatments (both progenitor and stem cells and additives to modify or repair cells), and any other medications, treatments or indicators that are useful when applied to specific areas within a patient, especially within the vasculature of a patient. In the method of the invention, the cells may include secretory cells which have been isolated from natural sources, or have been genetically engineered to produce neuroactive factors, growth factors, cytokines, antibodies, extracellular matrix components or neurohormonal agonists such as peptides or bioactive amines, precursors, active analogs, or active fragments. Preferred cell types may include all types of precursor or differentiated stem cells. Any cells that have been genetically engineered to express a neurotransmitter or its agonist, precursor, derivative, analog, or fragment which has similar neurotransmitter activity, or bioactive macromolecular factors, can also be used to practice this invention. For example, genetically engineered fibroblasts or other cell types may be used. Also expressly included are cells that secrete neuroactive factors and hormones, including "growth factors" such as described in U.S. Pat. No. 5,487,739 to Aebischer et al.

Neurotransmitters, neuroactive analgesic factors, as well as precursors, agonists, active analogs, and active fragments may be delivered using the device and method of the invention. Also included are proteins, nucleic acids and other macromolecules having biologic activity, as well as agents which might be infused for their physical or chemical properties. Examples of biologically active macromolecules could include growth factors, cytokines, antibodies, hormones, oligonucleotides, modified long DNA constructs (synthetic vectors), glycoproteins and glycolipids. Examples of agents which might be infused for their physical properties could include radiographic contrast agents or reagents to enhance the in vivo detection of implanted cells or the products they have been engineered to produce.

The catheter may comprise a coaxial (approximately coaxial) or coparallel multi-fluid flow chamber catheter having at least two concentric or two parallel chambers carrying fluid in the catheter, the at least two chambers comprising an outer chamber and an at least inner chamber. The outer chamber may comprise the first fluid pathway and the at least an inner chamber may comprise the second fluid pathway. In one embodiment, the catheter has a distal end first inserted into a patient and a proximal end, the catheter having a delivery portal and a capture portal, the delivery portal being closer to the proximal end of the catheter than the capture portal, so that captured fluid flows from a relatively distal region to a relatively proximal region within the at least inner chamber. In a second embodiment, the catheter has a distal end first inserted into a patient and a proximal end, the catheter having a delivery portal and a capture portal, the delivery portal being closer to the distal end of the catheter than the capture portal, so that captured fluid flows from a relatively proximal region to a relatively distal region within the at least inner chamber. There is ordinarily an internal transfer portal within the catheter that allows direct mass transfer of captured agent and fluid into the outer chamber, and at least some transferred captured agent and liquid is delivered through the delivery portal into the liquid environment. The method may operate with the catheter being positioned under non-invasive imaging guidance.

In general, the system uses a catheter system having a distal insertion end and a proximal end comprising: at least two internal liquid flow chambers comprising an outer liquid flow chamber and an at least one inner liquid flow chamber; the outer liquid flow chamber having a fluid delivery component for delivering fluid treatment material from the outer liquid flow chamber into a liquid environment within a patient, the liquid fluid treatment material moving from the proximal end towards the distal end to at least the fluid delivery component; the at least one inner liquid flow chamber having a fluid capture component for capturing liquid from the liquid environment that contains delivered fluid treatment material; the fluid capture component having a flow path such that captured liquid from the liquid environment is moved in a proximal direction before the fluid delivery component to a transfer component that enables transfer of captured fluid into the outer liquid flow chamber so that at least some transferred captured liquid introduced into the outer liquid flow chamber can be delivered through the delivery component into the liquid environment.

FIG. 1 shows a body part 1 (in this case a tubular structure such as a blood vessel) with a body fluid such as blood 2 flowing from right to left in the tubular body structure 1 in the direction of the arrow. A stenotic or neoplastic lesion 3 blocks or occludes part of the tubular body structure 1. A catheter 50 consists of an outer tube 4 with a flow region 4a and an inner tube 5 with an inner tube flow area 5a assembled such that the inner tube 5 is positioned approximately coaxially within the outer tube 4 and with the distal end 9 of the inner tube 5 either flush with or protruding slightly from the distal end 4b of the outer tube 4 at the distal end of the catheter 50. A therapeutic agent 6 is made to flow through the inside 5a of the inner tube 5 in such a way that the direction of the flow of the therapeutic agent 6 is anti-parallel to that of the body fluid 2 within the tubular body structure 1. A partial sealing ring, filter, structural support, flow control element or baffle 7 may also support part of the distal end of the inner tube 5 within the central barrel of the outer tube 4, and may assist in preventing fluids from refluxing through inter-tube gap and reaching the proximal end of the catheter 50. On the distal side (with respect to agent flow pattern) of the sealing ring or baffle 7, there may be a plurality of apertures 8 that allow mass transfer or diffusion communication between the inside 5a of the distal end of inner tube 5 and the inside 4a of the distal end of outer tube 4. The therapeutic agent 6 may exit the distal end 9 of inner tube and undergoes a degree of flow reversal along arrow path 11 (changing direction of integrated mass transfer) due to the presence of the flowing bodily fluid 2. Regions of circulation 10 are present proximal to the distal end 9 of the catheter 50. An internal (to the catheter) re-entrant flow path 12 travels through the inter-tube gap 4a and is coupled into the inside of inner tube 5 through the apertures 8 where the moving fluid (now comprising agent and blood) then undergoes another flow reversal of the flow of therapeutic agent 6, such that what is identified as a combined flow 13 then travels through and exits distal tip 8 of inner tube 5. The process can be continued until such time as the lesion 3 has been treated (e.g., dissolved) by the therapeutic action of the agent 6 or until the flow of the agent 6 has been stopped by the clinician treating the patient.

There are fluid dynamic considerations that can be made about the relative pressures within the various portions of the flow patterns surrounding and within the catheter. For example, at some point during the transfer of fluid from the inner tube gap 4d in the outer tube 4, the pressure within that outer tube gap 4d must be greater than the pressure immediately inside the inner tube gap 5a at the portal 8 to effect mass transfer. As some of the pressure at gap position 4d may be due to blood pressure, pressure control of the fluid immediately adjacent the portals may be consistently maintained between the systolic and diastolic pressure levels, or the pressure inside the inner tube gap 5a may be varied (pulsed) according to the pressure levels either sensed or anticipated in the pressure at 4d based upon blood pressure and pulse. For example, sensors (not shown) may be on the distal portion 9 of the inner tube 5 to determine blood pressure at the distal portion 9 of the inner tube 5, the pressure at distal portion 9 slightly anticipating or signaling the pressure passing to position 4d. Signals from the sensor (not shown) at the distal portion 9 of the inner tube 5 can be used to signal a system (not shown) that provides fluid pressure to the flow of agent 6 and the fluid immediate adjacent the portals 8.

Figure 2:
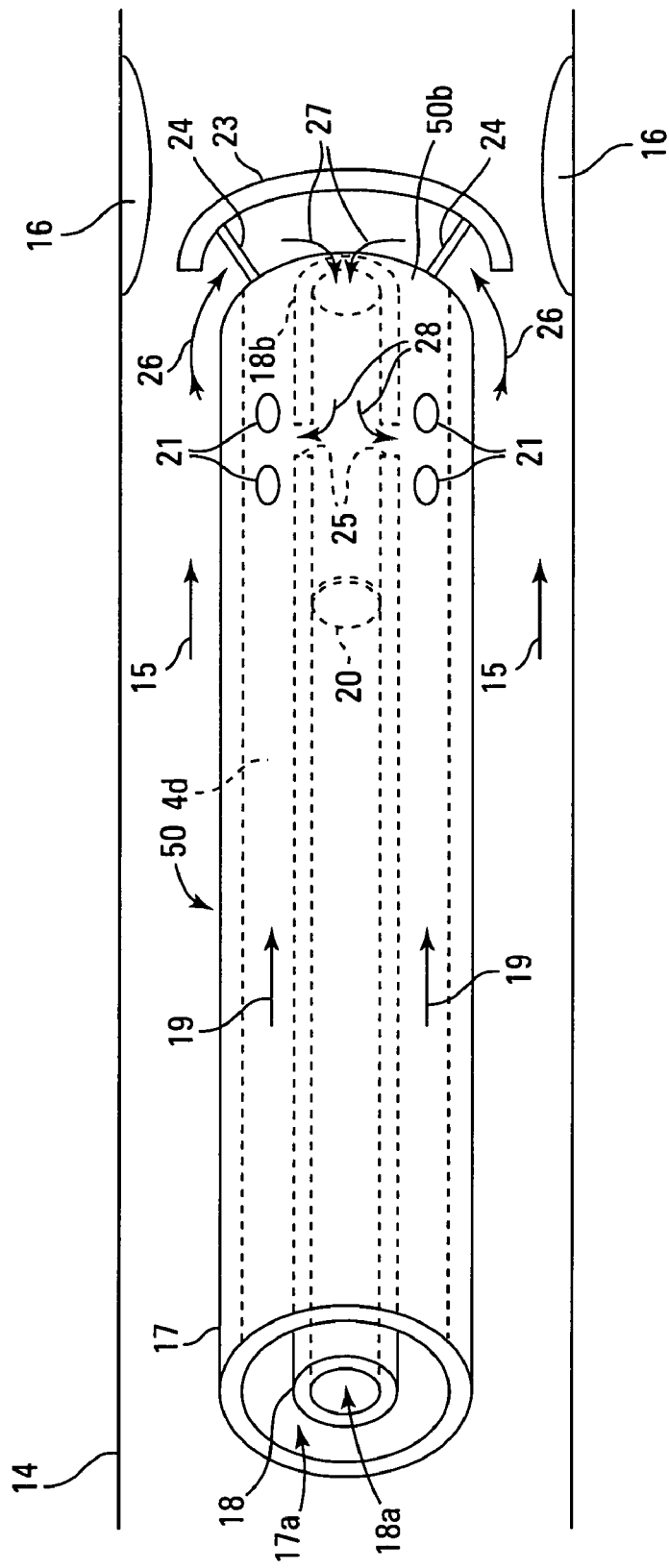
FIG. 2 shows an in situ assembly of one embodiment of a coaxial catheter means used to achieve recirculative delivery of an infused agent in the case where the direction of flow of the agent through the catheter means is parallel to that of the blood of the host vessel.

FIG. 2 shows a body part 14, for example in this case a tubular structure such as a blood vessel 14, with a body fluid such as blood 15 flowing from left to right (as shown by the arrows) in the tubular body structure 14. A stenotic or neoplastic lesion 16 is shown blocking or occluding part of the tubular body structure 14. A catheter 50 is shown comprising an outer tube 17 and an inner tube 18 is assembled such that the inner tube 18 is positioned approximately coaxially within the outer tube 17 and with the distal end 18b of the inner tube 18 either flush with or indented slightly within the outer tube 17 at the distal end 50b of the catheter 50. A therapeutic agent 19 is made to flow through the inter-tube gap 17a in such a way that the direction of the flow of the therapeutic agent is parallel to that of the body fluid 15 within the tubular body structure 14. A sealing plate or baffle 20 blocks or occludes the distal end of the inner tube 18 and prevents any fluids from refluxing through the inner tube and reaching the proximal end of the catheter 50. On the distal side of the sealing ring or baffle 20 there are shown a plurality of apertures 25 that allow mass transfer or diffusion transfer communication between the inside 18a of the distal end of inner tube 18 and the inside 17a of the distal end of outer tube 17. The therapeutic agent 19 exits through port holes 21 in the distal end of outer tube 17 where it comes into contact and mixes with the body fluid 19 and also comes into contact and acts on the lesion 16. An endcap 23 is held in place on the distal end of the catheter 50 by stand-offs 24 which create a region through which a fraction of the flow 26 is captured (as shown by arrows adjacent 26) and redirected through the end port 27 on the distal tip of the inner tube 18 of the catheter 50. The resulting flow 28 is recirculated back into the stream of the agent 19 via the apertures 25, thus permitting recirculation of the mixture of the therapeutic agent 19 plus the body fluid (e.g., blood) 15. The process can be continued until such time as the lesion 16 has been treated (e.g., dissolved) by the therapeutic action of the agent 19 or until the flow of the agent 19 has been stopped by the clinician treating the patient. Pressure consideration affecting mass transfer between fluid flows should be considered and/or controlled in a manner similar to that considered with respect to FIG. 1.

Figure 3:
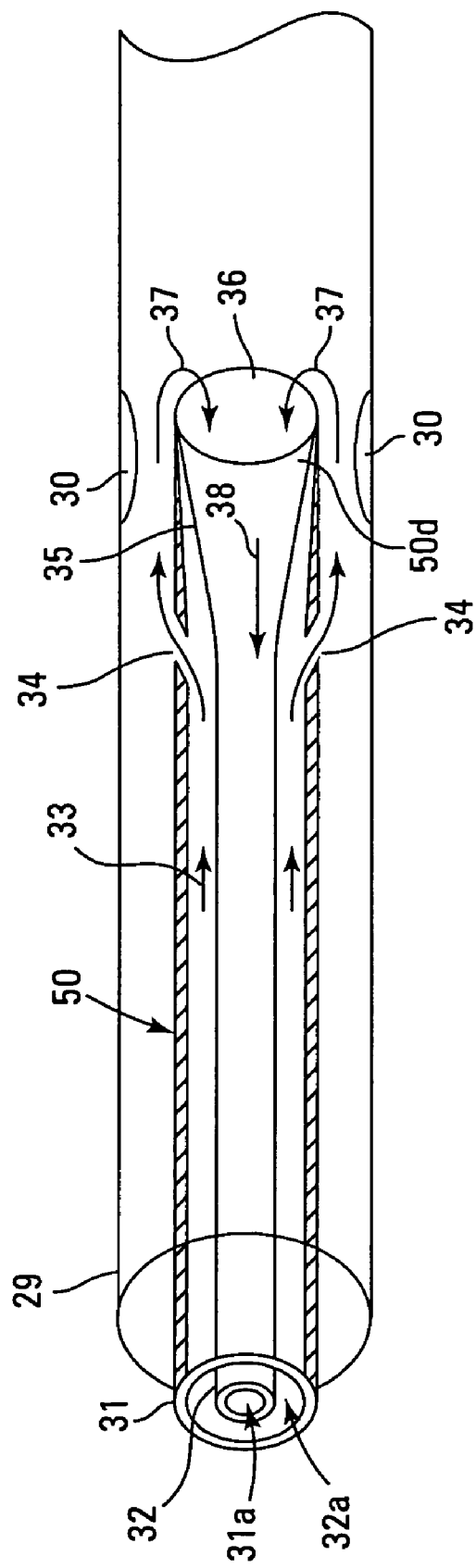
FIG. 3 shows one embodiment of a coaxial catheter means used to achieve recirculative delivery of an infused agent in the case where there is no flow of a bodily fluid in the body part into which the catheter means has been inserted.

FIG. 3 shows a body part 19, which, for example, might be either a hollow or parenchymal organ or a tubular body structure such as a blood vessel, in which there is a lesion 30, which might, by way of a non-limiting example, be a stenotic or neoplastic lesion. A coaxial catheter 50 comprising an outer tube 31 and an inner tube 32 is positioned inside of the body part 29 such that the distal end of the catheter 50 is located in the vicinity of the lesion 30. A therapeutic agent 33 is made to flow through the inter-tube gap 31a between the inside of outer tube 31 and the outside of the inner tube 32, and the agent 33 exits the catheter 50 through a plurality of apertures 34 at the distal end of the catheter 50. If there is no flow of any bodily fluid through the region surrounding the distal end 50d of the catheter 50, then some fraction of the fluid constituting the therapeutic agent 37 will dwell in the vicinity of the lesion 30 and mix with any fluids in that vicinity, and also carry out its therapeutic function, which might be to dissolve the lesion 30. The fluid 37, plus any debris from the lesion 30 can be aspiratively pulled into the orifice 36 at the distal end of the inner tube 32. The orifice 36 may be of approximately the same diameter as the diameter of the outer tube 31, due to an expansion of the diameter of the inner tube 32 as a result of the incorporation of the tapered section 35 of the inner tube 32. A flow path 38 of the fluid 37 plus debris from the dissolution of the lesion 30 can be extracted from the proximal end of the catheter 50, or the fluid 37 can be recirculatively pumped back through the inter-tube gap 32a along with the agent 33.

The catheter of the present invention can similarly be used for delivery of agents into the intracranial compartment, including the cerebral ventricles, cisterns, epidural and subdural spaces, sinuses and blood vessels; the spinal cord, including discs, nerves and associated vascular system; the heart and the coronary vascular circulation; liver and the hepatic vascular circulation; kidney and the intrarenal circulation; spleen and splenic vascular system; gastrointestinal system; special senses, including the visual system, auditory system, and olfactory system; endocrine system, including the pituitary gland, adrenal gland, testes and ovaries. For intracranial applications, the catheter is preferably made of a low friction material, such as various polymeric compositions including polyvinylchloride, polyacrylonitrile, polyvinylidene fluoride, polystyrene, polyurethane, or polyamide, so as to minimize abrasive damage to the brain during insertion. The catheter is also preferably visible under MR and CT imaging. Methods for improved passive MR visualization of implantable medical devices, such as catheters, are disclosed in U.S. Pat. No. 5,744,958 to Werne. Exemplary of methods for active MR visualization of implantable medical devices such as catheters is U.S. Pat. No. 5,211,165 to Dumoulin et al., and U.S. Pat. No. 6,061,587 to Kucharczyk et al.

Figure 4A:
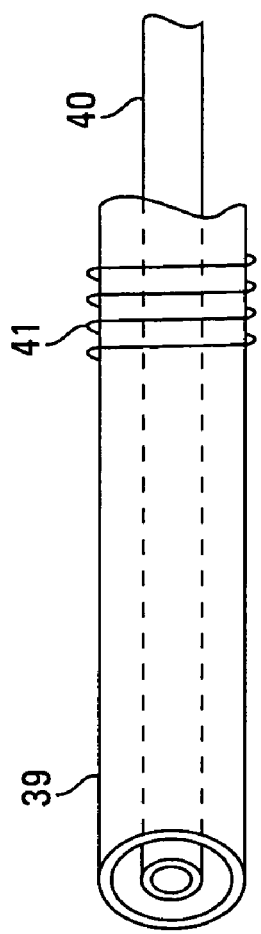
FIGS. 4A, 4B and 4C show three embodiments of microcoils as installed on a coaxial catheter means, for the purpose of enhancing magnetic resonance imaging capabilities during procedures involving the coaxial catheter means.
Figure 4B:
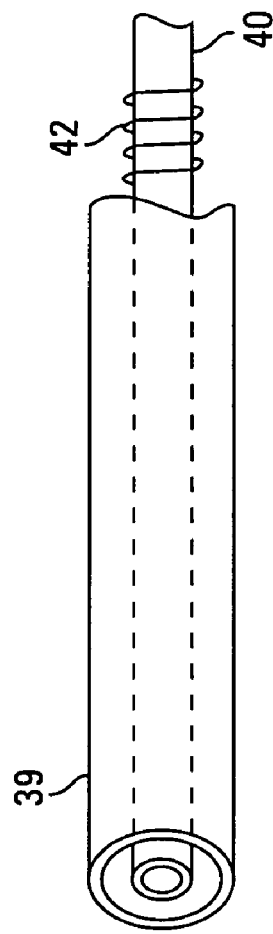
Figure 4C:
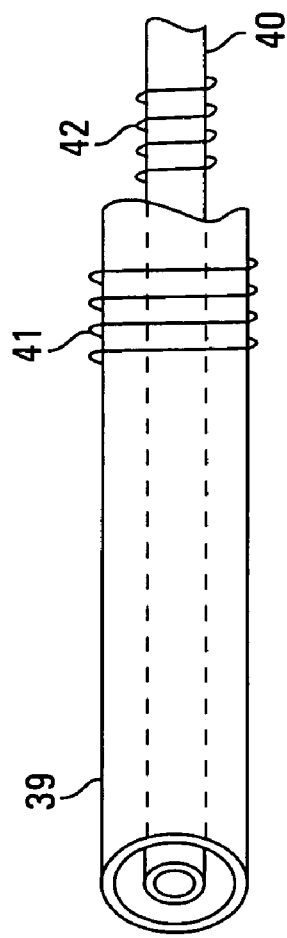

FIGS. 4A, 4B and 4C show coaxial catheter structures comprising an outer tube 39 and an inner tube 40. In FIG. 4A, a radio frequency (RF) microcoil 41 is wound circumferentially on the outer tube 39. In FIG. 4B, an RF microcoil means 42 is wound circumferentially on the inner tube 40. In FIG. 4C, an RF microcoil system 41 and 42 are wound circumferentially on both the outer tube 39 and the inner tube 40. The physical and electrical characteristics of the RF microcoil elements 41 and 42 are such as to enhance the contrast of magnetic resonance images made of body parts into which the catheter means incorporating the microcoil elements are inserted. Active MR visualization of drug, cell, and gene vector delivery can be achieved by means of one or more RF microcoils positioned on the catheter as disclosed in U.S. Pat. No. 6,026,316 to Kucharczyk and Moseley. Single microcoils may be used separately or the combination of microcoils may be constructed in an array that may be used together to optimally image the surrounding environment, including the tissue structure and function within the field of response of the microcoils. The system of microcoils may, by way of non-limiting example, be used for very small (picoliter, nanoliter or microliter) injections measured within a solenoid volume RF microcoil, which by design is mainly sensitive to the volume inside the coil. The imaging volume in such a use is usually directly related to the diameter of the RF coil.

Figure 5:
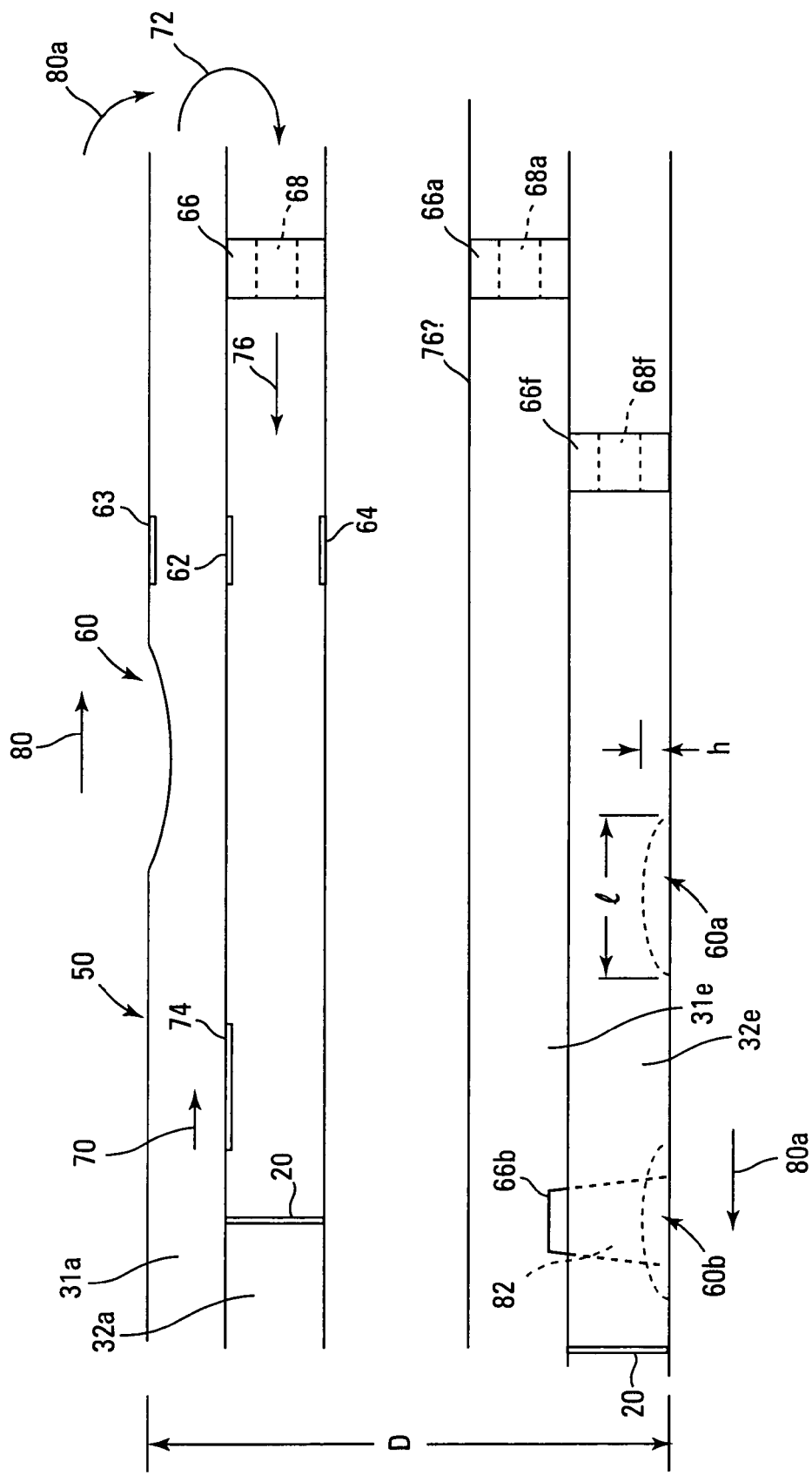
FIG. 5 shows a side view of a catheter that embodies a number of alternative structures and embodiments within a single exemplary structure.

FIG. 5 shows a side view of a catheter system 50 embodying a number of alternative features. The agent delivery liquid within outer tube channel 31a moves in a direction 70 past an opening or portal 60 in the catheter system 50. The dimensions of the opening may depend upon quite a few parameters that are within the skill of the artisan in assessing for each type of medical treatment proposed. Some relative proportions between the diameter D (and associated circumference) of the catheter system 50 tend to remain constant or at least within a reasonably comprehensible range. The portal 60 should neither be so long or so extensive about the circumference of the catheter system 50 as to weaken the catheter system 50 structure to a point where it becomes fragile. From a strictly engineering standpoint, unless some highly significant strengthening effort is made to the external walls of the catheter system 50 (as by reinforcement to the material of the wall, thicker material about the portal, and the like), the arc covered by the opening of the portal should remain less than 50% of the circumference of the catheter system 50, preferably less than 40%, preferably less than 34%, and more preferably less than 25, and less than 20% of the circumference of the catheter system 50. The larger the percentage of the arc, the greater tendency there is for the outer surface of the catheter system 50 to buckle under linear compression.

As the liquid flow 70 passes the portal 60, agent is released into the surrounding fluid flow path 80, which is parallel to the flow of agent delivery fluid 70. The mixture of external fluid and blood as flow path 80a at the end of the catheter system 50 can commingle with the recycling flow 72 of the liquid agent delivery stream into inner tube channel 32a. A pumping system 66 with a flow chamber 68 provides the pressure control desirable for directing the flow of liquids within the recycling system and moving recycling flow 76. A system of sensors (which may be little more than cathodes and anodes 62, 63 and 64 can be used to determine concentrations of agent within various streams to provide information to a processor (not shown) to drive the pump 66. As shown elsewhere, a communication link 76 (which could also be a wireless link) is connected to a second motor 66a and second flow chamber 68a. The pump 66 and 66a activity may be controlled based upon the readings taken by sensors that are material to desired results, such sensors possibly determining appropriate and inappropriate agent concentration ranges, flow rates, pressure levels, dissolved clot content in fluids, temperature, pH, and the like. Liquid may be passed from the inner channel 32a to the outer channel 31a through a vent 70, which may be controllable in an open/close or degree of opening sense. Another baffle 20 is shown to assist in flow control within inner channel 32a.

Although the simplest design for a catheter system according to these teachings would have the primary agent flow in the outer tube channel, an alternative construction shown in one section of FIG. 5 could also perform this function. As shown, portal 60e is connected by a narrow tube 82 through an outer tube channel 32e (carrying recycled material) to a pump system 66b that can move primary agent (non-recycled agent) from the inner channel 31e to the exterior fluid 80a. A pumping system 66f and flow path 68f would move captured agent/blood mixtures back into the outer recycling channel 32e for delivery through portal 60a or around open areas in portal 60b not closed off by the tube 66b. The relative length l and depth h of the portals have already been generally described. It should be noted that portal dimensions do not have to be uniform, even on the same catheter systems, but that sequential catheter portals may vary in size to assist in managing the relative flow in the primary agent delivery pathways and the recycling pathways.

As noted above, some identified systems of the prior art suffer from the limitation that the existing multi-lumen catheter designs do not describe pumping means and flow designs and flow controls for coordinately controlling emitting flow and recapture flow of agents, such as would enabling recirculative flow between the outside of an outermost lumen and the inside of an interior or innermost lumen. By providing independent pressure controlling systems (pumps, meters, barriers, and the like) in each lumen or portal, there is provided greater systemic control and relative control of flow, capture, reintroduction and emission of materials. These controls may be directed manually or automatically (using sensors to provide data upon which the automated systems can base changes in rates). For example, if the capture flow pressure is stronger than the emission flow pressure, the dwell time of deliver agent will tend to be shorter, and the concentration of actives in the captured liquid will tend to be higher. Interactive controls that sense the flow rates in the at least two lumens, access lookup tables in processors, and adjust the respective or relative flow rates (and possibly original concentrations in the higher concentration agent supply lumen) to assure compliance with intended diagnostic or treatment parameters.

It is to be noted that for convenience, the catheters and lumens and flows have been shown in linear format. It is understood in the practice of the present technology that the liquid environment (e.g., blood vessel) is not always reachable by a straight line path, but is more likely to encounter curves in its passage, and that the final targeted area where the catheter resides may require or desirably include that the catheter not be rigid and remain in a perfectly straight structure. It is therefore understood that the catheter may also possibly be flexible and may contain elastic memory of a curve for assistance with proper positioning within a targeted area having know geometries where a curvature might be useful is sitting the catheter in an optimized position.

As noted above, this Application is a continuation-in-part application of U.S. patent application Ser. No. 10/444,884, filed May 23, 2003 (U.S. 20030204171, published Oct. 30, 2003), which is in turn a division of U.S. patent application Ser. No. 09/574,857, filed May 19, 2000, now U.S. Pat. No. 6,599,274, which in turn claims priority from U.S. Provisional Patent Application Ser. No. 60/177,263. This Application independently claims additional priority from U.S. Provisional Application Ser. No. 60/561,571, filed Apr. 13, 2004. This Application also claims priority from U.S. patent application Ser. No. 10/957,538, filed Oct. 1, 2005, Titled Combined MR Coil Technology in Medical Devices. Each of these applications and patents is incorporated herein by reference.

One skilled in the art can see that many other embodiments of inner and outer tube means, port hole means, sealing rings, sealing plates and baffle means, endcap means, taper and distal port hole means, flow channeling and recirculation means, sensors, heating elements, and other details of construction and use constitute alternatives and variations within the scope of the disclosure provided herein for novel and insightful conceptual means, system and techniques which underlie the present technology.

We claim:

1. A method of diffusing liquid medical treatment agent by delivery to a region in a patient comprising: delivering the agent selected from the group consisting of diagnostic and therapeutic agents from a portal from a first fluid pathway in a catheter into a liquid environment within the patient; allowing the liquid agent to contact a targeted area of treatment within the patient; capturing at least some agent mixed with said liquid from the environment; returning at least some captured agent mixed with liquid from the enviromnent to a second fluid pathway in the catheter; and delivering at least some captured agent mixed with liquid from the environment outside of the catheter so that the captured agent is again delivered to the targeted area of treatment and after the captured agent is again delivered to the targeted area, the at least some captured agent diffuses into the liquid environment.

2. The method of claim 1 wherein the catheter comprises a coaxial catheter having at least two concentric chambers carrying fluid in the catheter, the at least two chambers comprising an outer chamber and an at least inner chamber and the medical treatment agent is selected from the group consisting of anti-inflammatory agents, clot dissolving agents, anti-clotting agents, vascular wall repair agents, antibiotics, cell treatments and medications.

3. The method of claim 2 wherein the at least an outer chamber comprises the first fluid pathway and the medical treatment agent is selected from the group consisting of antibiotics, progenitor cell treatments and stein cell treatments.

4. The method of claim 1 wherein the catheter has a distal end first inserted into a patient and a proximal end, the catheter having a delivery portal and a capture portal, the delivery portal being closer to the proximal end of the catheter than the capture portal, so that captured fluid flows from a relatively distal region to a relatively proximal region within the at least inner chamber.

5. The method of claim 4 wherein the catheter is positioned near the targeted area of treatment using non-invasive imaging guidance.

6. The method of claim 1 wherein the capture flow pressure from a portal performing the capturing of at least some agent mixed with said liquid from the environment is stronger than the emission flow pressure from the portal from the first fluid pathway.

7. The method of claim 1 wherein the agent is selected from the group consisting of neurotransmitters, neuroactive analgesic factors, agonists, proteins, nucleic acids, macromolecules having biologic activity, growth factors, cytokines, antibodies, hormones, oligonucleotides, modified long DNA constructs, glycoproteins and glycolipids.

8. The method of claim 1 wherein the catheter is positioned under non-invasive imaging guidance.

9. The method of claim 1 wherein the liquid agent comprises a liquid carrier and cells.

10. The method of claim 1 wherein the liquid agent comprises a solution of an agent.

11. The method of claim 10 wherein the liquid agent is free of a medically active number of cells.

12. A method of liquid medical treatment agent delivery to a region in a patient comprising: delivering the agent from a portal from a first fluid pathway in a catheter into a liquid environment within the patient; allowing the liquid agent to contact a targeted area of treatment within the patient; capturing at least some agent mixed with said liquid from the environment; returning at least some captured agent mixed with liquid from the environment to a second fluid pathway in the catheter; and delivering at least some captured agent mixed with liquid from the environment outside of the catheter so that the captured agent is again delivered back to the targeted area of treatment, wherein the captured agent again diffuses into the liquid environment after delivery wherein the catheter comprises a coaxial catheter having at least two concentric chambers carrying fluid in the catheter, the at least two chambers comprising an outer chamber and an at least inner chamber, wherein the at least an outer chamber comprises the first fluid pathway, wherein the at least an inner chamber comprises the second fluid pathway, wherein the catheter has a distal end first inserted into a patient and a proximal end, the catheter having a delivery portal and a capture portal, the delivery portal being closer to the proximal end of the catheter than the capture portal, so that captured fluid flows from a relatively distal region to a relatively proximal region within the at least inner chamber and wherein there is an internal transfer portal within the catheter that allows direct mass transfer of captured agent and fluid into the outer chamber, and that at least some transferred captured agent and liquid is delivered through the delivery portal into the liquid environment.

13. The method of claim 12 wherein the agent is selected from the group consisting of neurotransmitters, neuroactive analgesic factors, agonists, proteins, nucleic acids, macromolecules having biologic activity, growth factors, cytokines, antibodies, hormones, oligonucleotides, modified long DNA constructs, glycoproteins and glycolipids.

14. The method of claim 12 wherein the catheter is positioned under non-invasive imaging guidance.

15. The method of claim 12 wherein the catheter is positioned near the targeted area of treatment using non-invasive imaging guidance.

16. The method of claim 12 wherein the liquid agent comprises a liquid carrier and cells.

17. The method of claim 12 wherein the liquid agent comprises a solution of an agent.

18. The method of claim 17 wherein the liquid agent is free of a medically active number of cells.

19. The method of claim 12 wherein at least some transferred captured agent difftises after it is delivered into a patient.

20. The method of claim 12 wherein the at least an inner chamber comprises the second fluid pathway and the medical treatment agent is selected from the group consisting of antibiotics, progenitor cell treatments and stem cell treatments.

* * * * *